US008797398B2

(12) United States Patent
Drescher et al.

(10) Patent No.: US 8,797,398 B2
(45) Date of Patent: Aug. 5, 2014

(54) ON-THE-FLY DIMENSIONAL IMAGING INSPECTION

(75) Inventors: Joseph D. Drescher, Middletown, CT (US); Jesse R. Boyer, Manchester, CT (US); Robert E. Erickson, Storrs, CT (US); Erik M. Pedersen, Cheshire, CT (US)

(73) Assignee: United Technologies Corporation, Hartford, CT (US)

( * ) Notice: Subject to any disclaimer, the term of this patent is extended or adjusted under 35 U.S.C. 154(b) by 321 days.

(21) Appl. No.: 12/772,510

(22) Filed: May 3, 2010

(65) Prior Publication Data

US 2011/0267451 A1 Nov. 3, 2011

(51) Int. Cl.
*H04N 7/18* (2006.01)
*G06F 11/30* (2006.01)
*G21C 17/00* (2006.01)

(52) U.S. Cl.
USPC ............................................ 348/92; 702/185

(58) Field of Classification Search
USPC ............ 702/185; 382/8; 358/101; 348/92, 53
See application file for complete search history.

(56) References Cited

U.S. PATENT DOCUMENTS

| 4,807,296 | A | * | 2/1989 | Ando et al. ................... 382/151 |
| 5,125,035 | A | * | 6/1992 | McCarthy et al. ............ 382/141 |
| 7,489,811 | B2 | * | 2/2009 | Brummel et al. ............. 382/152 |
| 7,574,035 | B2 | | 8/2009 | Koonankeil | |
| 2005/0151963 | A1 | * | 7/2005 | Pulla et al. ................ 356/139.03 |
| 2007/0276629 | A1 | * | 11/2007 | Koonankeil ................... 702/185 |
| 2010/0188500 | A1 | * | 7/2010 | Bouchard et al. ............... 348/93 |

OTHER PUBLICATIONS

Conjunction. (2007). In the American Heritage® Dictionary of the English Language. Retrieved from http://www.credoreference.com/entry/hmdictenglang/conjunction.*

* cited by examiner

*Primary Examiner* — Joseph Ustaris
*Assistant Examiner* — Ellyar Y Barazesh
(74) *Attorney, Agent, or Firm* — Miller, Matthias & Hull LLP (57) ABSTRACT

A method and system are provided for inspecting a plurality of target features arrayed in spaced arrangement on a surface of a target object, such as but not limited to inspection of the location of cooling air holes in the surface of a turbine blade or vane.

20 Claims, 3 Drawing Sheets

ON-THE-FLY DIMENSIONAL IMAGING INSPECTION

FIELD OF THE INVENTION

This invention relates generally systems and methods for inspecting manufactured articles and more particularly to systems and methods for verifying features on a manufactured article, such as verifying cooling air exit hole location on a turbine blade or vane for a gas turbine engine.

BACKGROUND OF THE INVENTION

Gas turbine engines, such as those used to power modern aircraft, include a compressor for pressurizing a supply of air, a combustor for burning fuel in the presence of high pressurize, compressed air to generate and accelerate high temperature, high velocity combustion gases, and a turbine for extracting energy from the resultant combustion gases. The combustion gases leaving the turbine are exhaust through a nozzle to produce thrust to power the aircraft. In passing through the turbine, the combustion gases turn the turbine, which turns a shaft in common with the compressor to drive the compressor.

As the hot combustion gases pass through the turbine, various turbine elements, such as the turbine stator vanes and turbine rotor blades of the turbine, are exposed to hot combustion gases. In order to protect these turbine elements from exposure to the hot combustion gases, it is known to cool the turbine blades and vanes. In order to facilitate cooling of the blades and vanes, it is known to form the turbine blades and vanes with complex systems of internal cooling passages into which compressor bleed air, or another cooling fluid, is directed to cool the blade or vane. The cooling air exits the blade/vane through a system of holes arranged in such a manner that the exterior surface of the blade/vane is cooled, and is then passed out of the engine with the rest of the exhausted combustion gases.

In some turbine blade/vane embodiments, the cooling air exit holes are arranged in a specific pattern on various facets of the blade/vane airfoil to create a surface cooling film. The surface cooling film creates a layer of cool air, which insulates the airfoil from the hot combustion gases passing through the turbine. In order to ensure that the surface cooling film properly forms, various shaped exit holes are precisely located and bored at various angles on the surface of the airfoil. Thus, after manufacture it is necessary to inspect the blades and vanes to ensure the holes are properly positioned.

Conventional inspection systems include a fixture for holding the turbine blade/vane being inspected, a video camera, and a computer for controlling the inspection process and processing the video camera images. Generally, conventional inspection systems require inspection of each cooling hole from a gun-barrel view, which typically also requires the use of a five-axis coordinate measuring machine (CMM) for orientating the element and stepping the video probe from hole to hole. Since the turbine vanes and blades may, for example, have as many as 200 to over 300 cooling holes, each of which must be individually inspected.

Conventional inspection systems implement a step and stop process inspection, wherein the video camera is moved from hole location to hole location and positioned in a stationary relationship relative to the hole for a period of about 1.5 to 2.0 seconds before moving on to the next hole. This dwell time is needed for the video camera and the target hole to synchronize position for the video camera to image the target hole, and the computer to analyze the dimensional measurements and output results. The video camera has a low frame rate capability, typically only 30 frames per second. Typically, inspection of a single airfoil may take as long as ten minutes, depending upon the number of holes and also the time required in initial part probing. Part probing is required to properly position the part to be inspected in the workpiece fixture prior to initiating the actual hole inspection, which in conventional practice can take from about 1.5 minutes to over 3 minutes. Therefore, there is a need for improved methods and systems for more quickly determining the location of holes on the surface of a turbine airfoil.

SUMMARY OF THE INVENTION

A method is provided for inspecting a plurality of target features arrayed in spaced arrangement on a surface of a target object. The method includes the steps of: providing a fixture for holding the target object; providing a high speed camera; selectively positioning at least one of the holding fixture and the high peed camera relative to the other in a continuous relative motion along a three-dimensional path over a plurality of selected target features without pause; and each time the high speed camera orientates to a selected target feature, capturing an image of the selected target feature during an exposure duration using the high speed camera while in relative motion. The method may include the step of providing a position manipulator in operative association with the holding fixture for selectively positioning the holding fixture to orient a feature to be imaged on the target object to a desired orientation to the high speed camera at each selected target feature along the three-dimensional path. The method may include the step of storing the captured image in a data archive and processing the captured image in parallel with relative movement of the high speed camera and the holding fixture from the imaged target feature to a next to be imaged target feature.

An inspection system is provided for inspecting a plurality of target features arrayed in spaced arrangement on a surface of a target object. The inspection system includes a position manipulator having a fixture for holding the target object, a high speed camera having an exposure duration of less than three millisecond, a light array in operative association with the high speed camera, a controller operatively associated with the high speed camera and with the position manipulator and operative to coordinate simultaneous positioning of the high speed camera and the target object in continuous relative motion along a three-dimensional path over the plurality of target features, and a processor operatively associated with the high speed camera for processing an image of a target feature received from the high speed camera. In an embodiment the position manipulator may comprise a five degrees of freedom CNC machine for manipulating the holding fixture in response to commands from the controller. The high speed camera may be a video camera having a frame rate capability of at least about 300 frames per sec. In an embodiment, the high speed camera may be a video camera having a frame rate capability of at least about 1000 frames per second. The light array may include a plurality of light emitting diodes and a LED driver operatively associated with the light emitting diodes for selectively switching the light emitting diodes from zero to full power in less than about 1 microsecond.

A method is provided for inspecting a turbine airfoil for measuring the location of at least of a plurality of selected holes of a multiplicity of holes arrayed in spaced arrangement in a surface of the turbine airfoil. The method includes the steps of: providing a position manipulator having a fixture for holding the turbine airfoil and having a five degrees of freedom positioning system for selectively positioning the holding fixture to orient the turbine airfoil; providing a high speed camera; providing a plurality of light emitting diodes in operative association with the high speed camera; selectively positioning at least one of the holding fixture and the high peed camera relative to the other in a continuous relative motion along a three-dimensional path over a plurality of selected target features without pause; and each time the high speed camera orientates to a selected target feature, powering the light array to illuminate the selected target feature at least for the exposure duration of the camera and capturing an image of the selected target feature during the exposure duration using the high speed camera while in relative motion with respect to the selected hole. The step of selectively positioning at least one of the holding fixture and the high speed camera relative to the other includes the step of simultaneously moving the high speed camera and repositioning the holding fixture in relative motion. The high speed camera may have an exposure duration of less than about 3 milliseconds. In an embodiment, the high speed camera comprises a video camera having a frame rate capability of at least 300 frames per second and in relative motion with respect to a selected hole to be imaged at a relative speed of at least 50 inches per minute. In an embodiment, the holes of the turbine airfoil are inspected at a rate of at least 2 holes per second. The method may also include the step of probing the position of the turbine airfoil within the fixture, including the steps of: setting a nominal location and orientation of a turbine airfoil loaded into the CNC machine to what was found as an actual location and orientation of a most previous turbine airfoil inspected; and initially probing a selected a single point on the turbine airfoil to establish an estimate of the turbine airfoil location along the part Z-axis.

BRIEF DESCRIPTION OF THE DRAWINGS

For a further understanding of the disclosure, reference will be made to the following detailed description which is to be read in connection with the accompanying drawing, where.

DETAILED DESCRIPTION OF THE INVENTION

Figure 1:
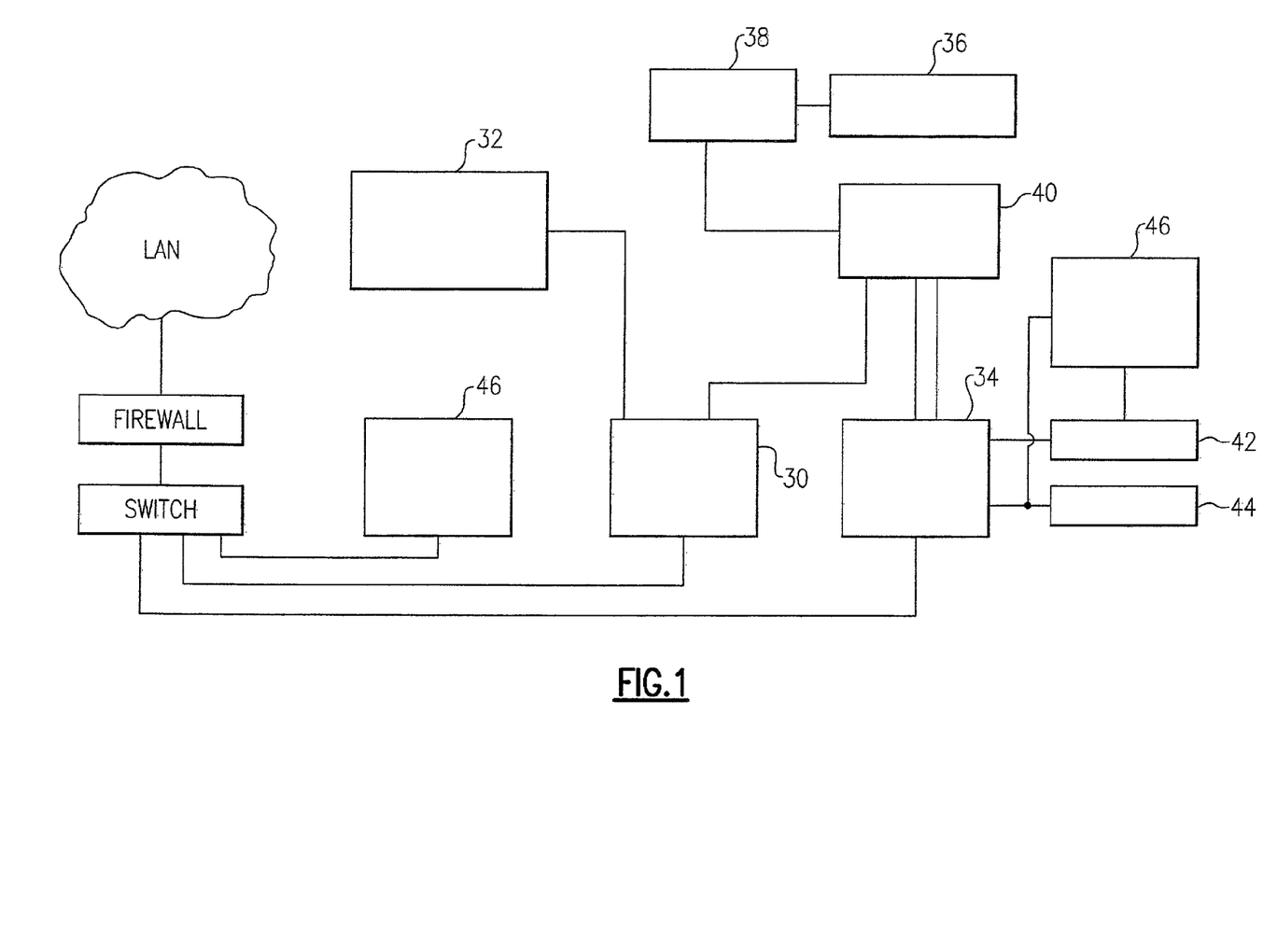
FIG. 1 is a block diagram schematic illustrating an exemplary embodiment of an inspection system for on-the-fly inspection of a plurality of target features associated with a part to be inspected.

There is depicted schematically in FIG. 1 an exemplary embodiment of an inspection system 20 for quickly and accurately locating the position of multiple target features associated with an object to be inspected. For example, the inspection system 20 disclosed herein may be used and the method of inspecting disclosed herein implemented in connection with the inspection of a turbine airfoil 22, such as a turbine blade or vane shown in FIG. 2, for the purpose of verifying the actual location of each of a multiplicity of cooling air exit holes 24 opening on the surface 26 of the turbine airfoil 22. It is to be understood, however, that the inspection system and the method for inspecting disclosed herein may be adapted for locating other features on other objects.

Referring now to FIG. 1, the inspection system 20 includes a fixture 28 for holding the target part (not shown in FIG. 1) being inspected, a fixture position manipulator 30, a controller 32, a processor 34, a light array 36, a light array driver 38 and a high speed camera 40. The holding fixture 28 secures the target part to be inspected in a specific position relative to the holding fixture such that each part in a series of similar parts to be inspected is held in substantially the same position within the holding fixture 28 from part to part. The holding fixture 28 is secured to the fixture position manipulator 30 in a fixed position. The light array 36 is operatively associated with the high speed camera 40 and positioned for providing light on the target part to facilitate imaging of the part by the high speed camera 40. The light array driver 38 is operatively associated with the light array 36 for powering the light array 36 to illuminate the target part. The controller 32 is operatively associated with the fixture position manipulator 30 for commanding the fixture position manipulator 30 to selectively position the holding fixture 28 to orient the target part whereby the selected target feature to be imaged is in a desired orientation relative to the high speed camera 40. The controller 32 also controls positioning of the high speed camera 40 and coordinates the triggering of the high speed camera 40 with the orientation of the target feature such that the high speed camera 40 is triggered and the target feature imaged when the high speed camera is in a gun barrel shot position with respect to the selected target feature. By gun barrel shot position/alignment, it is meant that the focal point of the high speed camera 40 is aligned along a line extending normal to the surface of the target object at the location of the target feature to be imaged.

The inspection system 20 is capable of implementing an on-the-fly inspection process in accord with the method disclosed herein. In operation, the controller 32 controls positioning of the target part by manipulation of the fixture position manipulator 30 in a controlled coordinated manner with movement of the high speed camera 40 whereby continuous relative movement along a specified, arbitrary three-dimensional path over the plurality of selected target features to be imaged is maintained between the high speed camera 40 and the target part as the multiplicity of target features are imaged without pause. That is, the high speed camera does not stop and dwell over any target feature location during imaging of that location on the target part. Rather, in accord with the process disclosed herein, the high speed camera 40 and the selected target feature to be imaged are in relative motion at a constant speed as the high speed camera is triggered and images the selected target feature. By eliminating the dwell time over the part at each inspection site, the inspection time associated with inspecting an individual target feature, such as a cooling air hole on a turbine airfoil, is significantly reduced relative to the conventional step and stop inspection method.

In on-the-fly inspection as disclosed herein, the movement of the target feature of interest relative to the high speed camera 40 over the duration of the frame capture must be less than a reasonable fraction, such as for example $1/10^{th}$, of the true position tolerance of the target feature. Thus, in implementing the on-the-fly inspection method disclosed herein, the speed of movement of the high speed camera 40 is primarily limited by the frame rate capability, of the camera 40 and the ability of the high speed camera 40 to collect enough light during the exposure duration for adequate contrast so that the image of the target feature can be resolved. Generally, the high speed camera 40 should have an exposure duration, i.e. time required for imaging a target feature, of less than three (3) milliseconds. For example, a high speed camera having a frame rate capability of at least about 300 frames per second would enable imaging with relative motion between the camera and the target feature at a constant speed of at least about 50 inches per minute.

The light array 36 is provided for illuminating the target feature with sufficient light at least during the exposure duration, that is at the time the high speed camera 40 images the target feature. The light array 36 comprises a plurality high intensity light emitting devices, for example light emitting diodes (LEDs), arranged to illuminate the target feature to provide adequate contrast. The number of light emitting diodes comprising the light array 36 depends upon the power level applied to drive each diode. If a higher power level is applied per diode, for example about one watt or more per diode, the number of light emitting diodes may be decreased. Conversely, if a lower drive power level per diode is desired, a greater number of light emitting diodes may be provided. However, conventional low power, i.e. low wattage, LEDs commonly used in commercial applications do not provide sufficient light output per diode to be used in implementing the on-the-fly inspection method disclosed herein. The number of LED's may also be reduced if a means of focusing is provided in association with the light emitting devices forming the light array 36 to increase the flux (intensity per unit area) in the image field of view of the high speed camera 40. The LED's making up the light array 36 may be arranged in a ring pattern, in a single row, a double row or any other suitable arrangement.

The light array driver 38 is controlled by the controller 30 through the high speed camera 40 to power the light emitting devices comprising the light array 36. Although the light array could be powered continuously during the inspection process, doing so creates excess heat and shortens the life of the lights. In implementing the method disclosed herein using a high speed camera, the light array 36 may be powered in synchronization with the imaging of the target feature by the high speed camera 40. When the high speed camera 40 is moving over the target feature, the high speed camera 40 triggers the light driver 38 to power the light array 36 to illuminate the target feature during the exposure duration. With LEDs making up the light array 36, the light driver 38 comprises a LED driver having the capability of selectively switching the light array LEDs from zero power to at least full power in less than one microsecond to flash the LEDs in coordination with the camera exposure duration. Precise coordination of the camera exposure duration and the LED flash duration is particularly important at the higher relative speeds of movement between the high speed camera 40 and the target feature to be imaged that may be used in implementing the on-the-fly inspection method disclosed herein to eliminate blurring and ensure clarity of the image of the target feature.

Additionally, the LED driver can have the capability of over-powering the light array LEDs, that is powering individual LEDs of the light array 36, all or selected LEDs thereof, at a power level in excess of the full rated power of the LED. Although over-powering the LEDs is not required when implementing the on the-fly inspection method disclosed herein, over-powering the LEDs produces a "strobing-like" effect that may improve image contrast and clarity during the exposure duration. This effect is not possible to attain with conventional lights, such as incandescent or halogen lights. The light array LEDs are arranged such that directional control is available for adjustment of the geometry comprising the orientation of the optical axis of the camera lens, the light from the LEDs, and the target part orientation surrounding the feature of interest. Adjustment may be achieved by selectively controlling, through software control, the intensity of each available light array LED at its respective location with respect to the target feature.

As noted previously, conventional step and stop inspection systems typically employ a 5-axis, coordinate measurement machine in combination with a low speed video camera. Such machines can move the video camera and/or the part to a location and orientation very well in a step and stop inspection process even though each axis may arrive at its individual target location at a different time. However, conventional coordinated measurement machines do not have the ability to control three linear and two rotary axes in a coordinated fashion for imaging while in motion as required in implementation of the on-the-fly inspection method disclosed.

In the on-the-fly inspection system 20, the fixture position manipulator 32 comprises a computer numerically controlled (CNC) machine under direct control of the controller 30. The CNC machine 32 secures the fixture 28 that holds the target object to be inspected. The CNC machine 32, under the control of the controller 30, provides coordinated five degree of freedom motion control for maneuvering the fixture 28 in the CNC machine 32 to align the target object to a desired orientation with the high speed camera 40 for imaging of the selected target feature. CNC machines with coordinated 5-axis motion control are known for use in the aerospace industry for machining applications, for example where the location and orientation of a cutting tool relative to the workpiece is important at all times when the two are in contact. However, the use of CNC machines with coordinated five degrees of freedom motion control is novel in inspection applications for imaging a target feature on a target object with a high speed camera while in relative motion along a three-dimensional path without the stop and step required in practice.

As noted above, in on-the-fly inspection as disclosed herein, the high speed camera 40 images the target feature while in relative motion with respect to the selected target feature at a constant speed. Depending upon the relative speed and the spacing between target features, the high speed camera 40 may be imaging several target features a second. Therefore, the inspection system must be capable of handling the images produced in such a manner as to not adversely impact control loop cycle time of the controller 30. During a single control loop cycle, the computer 34 will receive a signal from feedback devices of each axis as the actual position, modify this position of each axis with any active corrections as applicable, compare the result to the commanded position at that time, and output power signals to each axis motion control device (usually a motor) associated with the fixture position manipulator 32 subject to the various control parameters (tuning) which have been set. The control loop cycle time should desirably be around 1 millisecond or less. Performing analysis of images and performing other output functions during the "random" cycles when the images are available (1 in 150 cycles for example) in such a way that the cycle time can be maintained reliably would severely limit what the cycle time could be achieved and consequently severely limit the speed of measurements.

Accordingly, the inspection system 20 incorporates a parallel processor 34 for performing image analysis. Whenever the high speed camera 40 images a target feature, the single frame image is captured by the high speed camera 40 and stored to memory as a file in data archive 42. The processor 34 will access the image file, read the image file, analyze the image, determine the location of the target feature, for a hole center, and create the output data while the high speed camera and target object are in motion to align on the next target feature of interest. In conventional stop and step inspection methods, the image analysis was performed while the video camera remained stationary in front of the imaged target feature. In the on-the-fly inspection method disclosed herein, the image analysis occurs while the high speed camera and the target object are in relative motion along a three-dimensional path at its constant speed as the next target feature is brought into a gun shot barrel align with the high speed camera. Therefore, image analysis does not adversely impact control loop cycle time. If desired, an additional processor 46 may be provided in parallel with the processor 34 to assist in processing the images. Each of the processors 34 and 46, as well as the controller 30, may be commercially available microprocessors, each of which is typically associated with a separate computer monitor, memory bank and peripherals, but two or more of which may be associated with a common computer monitor, memory bank and peripherals, if practical from a logistics and processing viewpoint.

Figure 2:
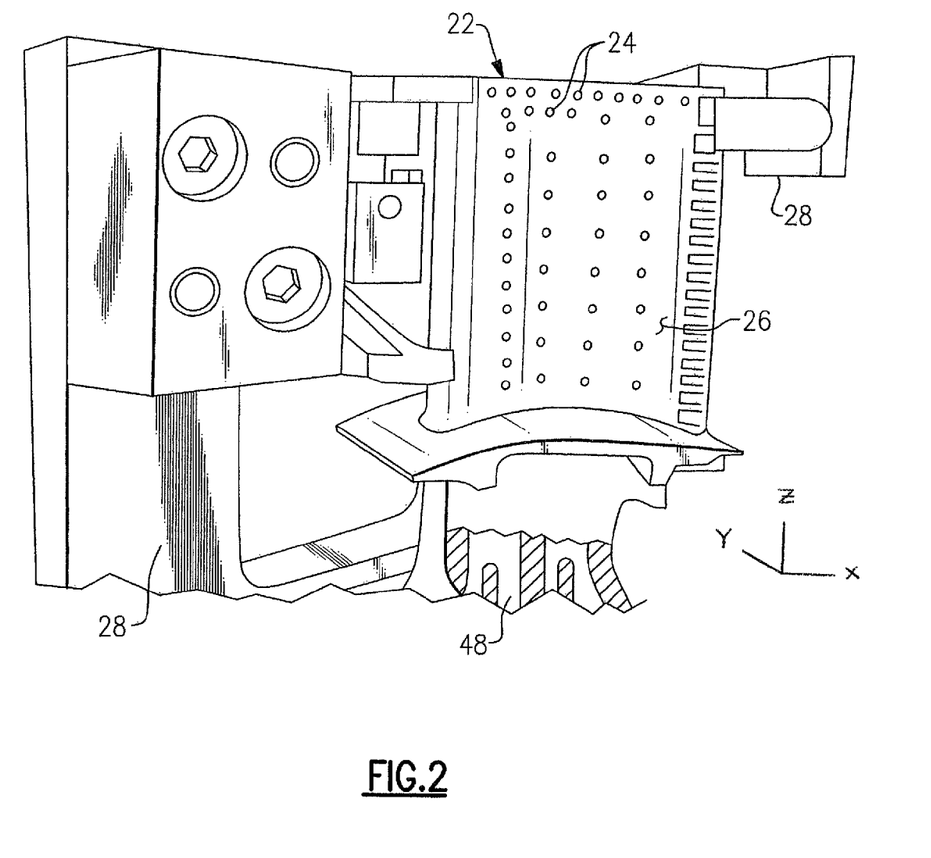
FIG. 2 is a partially cut-away elevation view of the pressure side of a turbine having a multiplicity of cooling air holes.

The on-the-fly inspection method will be described further as implemented for the inspection of turbine airfoils for the purpose of verifying the position of a multiplicity of cooling air holes. Referring to FIG. 2. there is depicted an exemplary embodiment of a turbine airfoil 22 having a multiplicity of cooling air exit holes 24 arranged in a generally column and row fashion on the pressure side surface 26 of the airfoil 22. The root or bottom of the airfoil 22 is shown in cut-away to reveal cooling air passages 48. To cool the turbine airfoils during operation of the gas turbine engine, high pressure air, typically compressor bleed air, enters the cooling passages 48, which extend into the interior of the turbine airfoil 22. At least a portion of the cooling air exits from the cooling air passages 48 through the cooling air exit holes 24 to flow along the exterior surface of the turbine airfoil 22. The multiplicity of cooling air exit holes 24 must be arranged in a precise pattern designed to achieve complete cooling coverage of the surface of the turbine airfoil 22. In an exemplary embodiment of a turbine airfoil, over 300 cooling air exit holes 24 may be provided with the cooling air exit holes 24 typically having a diameter of about 300 microns and typically being spaced apart at about 0.200 inches.

The on-the-fly inspection method disclosed herein can be used for verifying the precise actual location of each cooling air exit hole 24 on the turbine airfoil 22. To begin, through the user interface 50, which may be a dedicated computer terminal or a computer terminal in a network system, the operator selects the appropriate program for the turbine airfoil (blade or vane) to be inspected from a list of available part programs. The airfoil to be inspected, for example turbine airfoil 22, is loaded in a known manner in the fixture 28 of the fixture position manipulator 32, which in this implementation of the method comprises a five degree of freedom CNC machine. The high speed camera 40 and the holding fixture 28 are supported in the CNC machine 32 in spaced, facing relationship. The high speed camera 40 may be supported for movement in one or two linear degrees of freedom, while the holding fixture 28 is supported for movement in both rotational degrees of freedom and at least one linear degree of freedom. In a typical installation, the high speed camera 40 would be supported above the fixture and at least moveable along a vertical axis up and down relative to the turbine airfoil held in the holding fixture 28. With a turbine airfoil loaded onto the CNC machine 32, the location and orientation of the turbine airfoil with respect to each of the five degrees of freedom of the CNC machine 32 can be estimated based on the design of the holding fixture 28. As in conventional systems, the design of the holding fixture 28 includes the fixing of the turbine airfoil 22 to the holding fixture 28 in a repeatable consistent manner from airfoil to airfoil as well as the means of fixing the holding fixture 28 to the CNC machine 32 in a consistent manner.

It is possible, but not feasible, to know the location and orientation of the turbine airfoil with respect to the CNC machine to a level of accuracy required for the measurement of feature locations. This is due to the influence of variations that arise from actual dimensions of the turbine airfoil and holding fixture within their respective machining tolerances as well as the non-repeatability of airfoil loading and fixture loading. Because of the careful design and process controls that would be required to position the part deterministically to within the required limits, a touch-trigger probe is used to simply find the actual location and orientation of each individual turbine airfoil prior to its measurement. The part datum planes are established by measuring the location of 6 specific points on the surface of the turbine airfoil.

In conventional practice for hole inspection on turbine airfoils using the step and stop method, the accurate determination via part probing usually involves multiple iterations of the 6-point probing sequence for which each successive sequence improves accuracy in the determination of the part location and orientation. Iterations are required due to curvature on the surface in the vicinity of the specified datum points. If there is no curvature of the surface in the vicinity of the datum points, it is feasible to find the location and orientation of the part in one iteration of the probing sequence. In existing applications, part probing consumes from 1/10 to 1/3 of the total measuring time. It is a fixed time so the percent of total depends on the number of holes to be inspected, which is the variable time depending on individual part program.

However, if the same conventional part probing methods were to be used when implementing the on-the-fly inspection method disclosure herein for turbine airfoil cooling air hole inspection, the part probing portion of the measurement cycle could be expected to approach 75% even when a turbine airfoil has a relatively high number of holes to be inspected. Therefore, to shorten overall inspection time and take full advantage of the time saving associated with on-the-fly inspection, when implementing the on-the-fly inspection method the nominal location and orientation of a turbine airfoil loaded into the CNC machine 32 will be what was found as the actual location and orientation of the most previous turbine airfoil inspected, thereby reducing the potential variation to only the repeatability of the part loading and the variation within tolerances of the locating surface of the part. Additionally, the touch-trigger probe to be used will consist of two distinctly calibrated positions. The first position being the sphere as the end of the stylus and the second position being the cylinder of the stylus shaft itself at a specified location up from the sphere center. When the calibrated cylindrical portion of the probe is used on a surface datum point having curvature, it creates a line/point contact and eliminates errors due to curvature in one direction. Further, prior to initiation the probing sequence of the 6 datum points, a single point will be probed to establish a very good estimate of the turbine airfoil location along the part Z-axis. These changes will reduce the required probing to a single iteration for most parts and reduce the probing time from around 100 seconds associated with conventional probing practices to less than 50 seconds.

Figure 3:
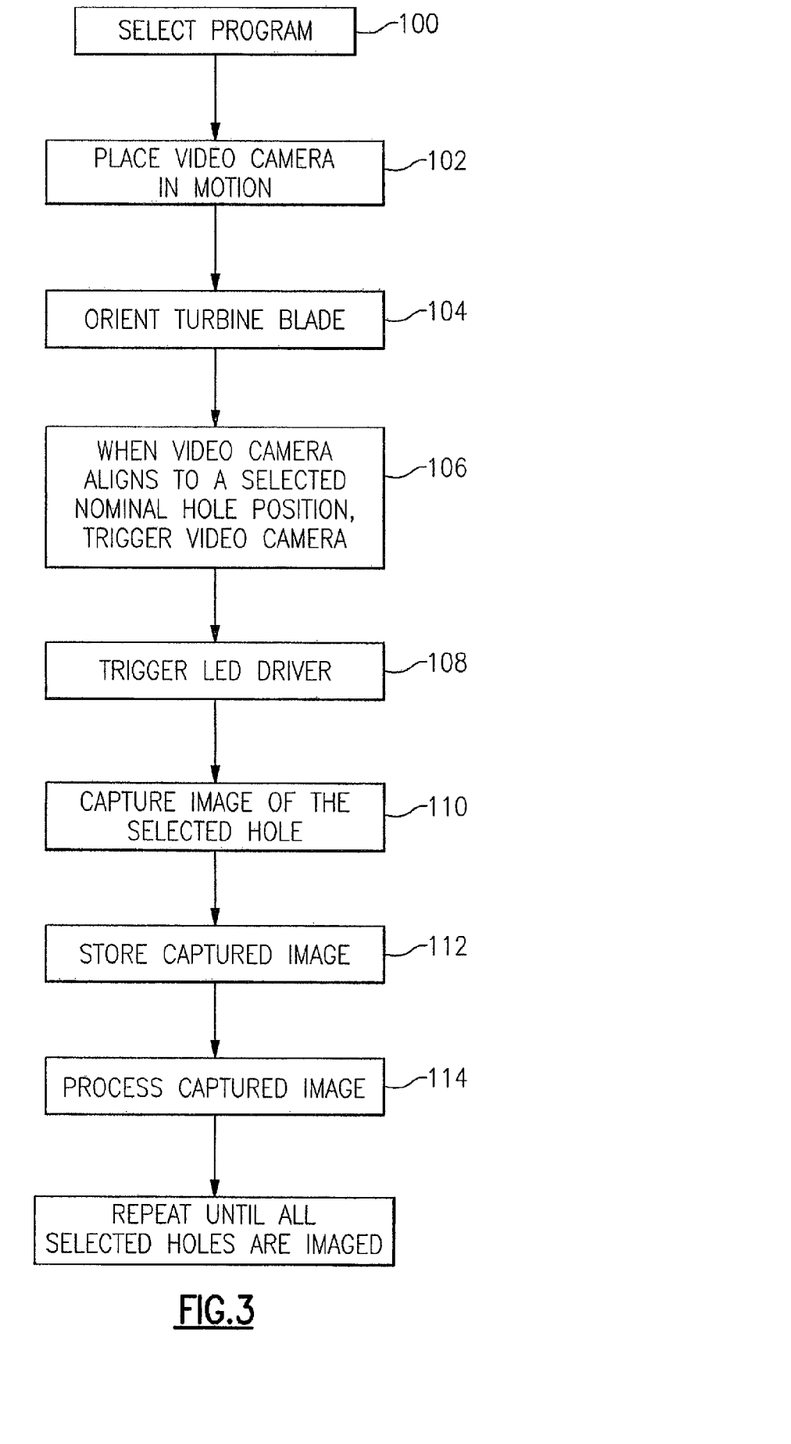
FIG. 3 is a flow chart illustrating a method for on-the-fly inspection in accord with an aspect of the invention.

Referring now to FIG. 3, when the operator selects the appropriate program associated with the turbine airfoil to be inspected, at step 100, the selected program will be loaded into the controller 30. The program will consist mainly as a list of positions for each of the 5 degrees of freedom associated with the CNC machine 32, i.e. 3 linear degrees of freedom (x, y and z coordinate axes) and two rotational degrees of freedom (one about the axis of the holding fixture and one in a plane orthogonal to the axis of the holding fixture). These positions correspond to the nominal locations of the holes to be inspected. The camera settings for the high speed camera 40, which in this implementation of the method disclosed herein comprises a video camera, are configurable by the data link with the controller 30. When a part program is selected, the controller 30 will make the previously specified settings on the video camera for that particular part program.

The actual inspection cycle begins with the computer 30, at step 102, placing the video camera 40 in motion and, simultaneously at step 104, maneuvering the fixture 28 holding the turbine airfoil. The video camera 40 and turbine airfoil are in relative motion along a three-dimensional path at a constant relative speed to orient the turbine airfoil and the video camera such that the next to be imaged target hole and the video camera are brought into gun barrel shot alignment. For example, the video camera and the turbine airfoil may be in relative motion along a three-dimensional path at a constant relative speed of at least about 50 inches per minute between holes in a row/column of holes 24 and at an even higher relative speed, for example about 200 inches per minute, between rows/columns of holes 24. The controller 30 controls the CNC machine 32 to maneuver the fixture 28 and relative movement of the video camera to properly orient the turbine airfoil 22 with respect to the video camera 40 for imaging of each individual hole 24 of the multiplicity of cooling air holes 24 on the surface of the turbine airfoil 22.

At step 106, at each instant during the inspection cycle that the video camera 40 aligns in gun barrel shot relationship to a nominal hole position, the controller 30 sends a signal to the video camera 40. At step 108, upon receipt of that signal from the controller 30, the video camera 40 triggers the LED driver 38 which in turn powers, that is switches from zero power to full power, the LEDs of the light array 36 for a preset duration. At step 110, in synchronization with the flashing of the LEDs of the light array 36, the video camera 40 captures an image of the target hole 22 as the video camera passes over the target hole.

At step 112, the captured image is stored in a designated folder in the data archive 42 associated with the processor 34. At step 114, the captured image is accessed and processed in parallel with the movement of the video camera 40 and the maneuvering of the fixture 28 while repositioning at a constant relative speed toward the next target hole. The basic result of an image analysis will be the pixel location of the centroid of the identified blob (Binary Large OBject), i.e. the cooling air exit hole 24. Based on previous calibration the location and rotation of the camera pixel array is known with respect to the machine coordinate system. Also, the location and orientation of the part coordinate system is known with respect to the machine coordinate system by the nominal tool design and by the results of the part probing which refines the tool matrix to actual. Furthermore, the location and orientation of each hole 24 is specified by the engineering definition for the part with respect to the part datum planes. Appropriate coordinate transformations are carried out by the processor 34 to determine the location of each hole 24 relative to that hole's nominal, specified location. The difference is the true position error.

The on-the-fly inspection method disclosed herein is capable of performing a hole location inspection of a turbine airfoil several times faster than the time required for using conventional step and stop hole inspection methods. For example, a turbine vane having 211 holes was subject to hole measurement inspection using a conventional step and stop method using a video camera having a frame rate capability of 30 frames per second. The time required to measure all of the 211 holes was timed at 443 seconds. Implementing the on-the-fly method disclosed herein using a high speed video camera having a frame rate capability of 1000 frames per second and moving the video camera and maneuvering the orientation of the turbine airfoil at a constant relative speed of 50 inches per minute between holes in a row and at a speed of 200 inches per minute between rows, it is estimated the measurement time for measuring the same 211 holes would be reduced to 43 seconds, a ten-fold decrease. As a further example, a turbine airfoil having 330 holes was subject to hole measurement inspection using a conventional step and stop method using a video camera having a frame rate capability of 30 frames per second. The time required to measure all of the 330 holes was timed at 690 seconds. Implementing the on-the-fly method disclosed herein using a high speed video camera having a frame rate capability of 1000 frames per second and moving the video camera and maneuvering the orientation of the turbine airfoil at a constant relative speed of 50 inches per minute between holes in a row and at a speed of 200 inches per minute between rows, it is estimated the measurement time for measuring the same 330 holes would be reduced to 57 seconds, an over ten-fold decrease.

Due to the dynamics of the CNC machine and the timing of electrical components, the on-the-fly inspection method discussed herein may not be quite as accurate in determining actual hole location on turbine airfoils as the conventional stop-and-dwell inspection method. However, the synergistic effect of the combination of the high speed camera, the five degree of freedom CNC machine, the LED light array and the controller for coordinating the relative motion along a three-dimensional path between the high speed camera and the turbine with the triggering of the high speed camera to image the holes while in relative motion, provides for a much faster inspection method, more than offsetting a slight difference in accuracy. Furthermore, any slight deficiency in accuracy compared to the conventional "stop and dwell" method may be compensated for on a part by part basis.

For example, for each unique part number to be inspected, a master part is identified as a calibrated artifact. The master part is then measured on a conventional inspection apparatus in accord with a conventional "stop and dwell" method. The master part is also measured on an inspection system implementing the "on-the-fly" inspection method disclosed herein. The respective hole dimension results attained by the two methods are compared for each and every measured hole location. A table of the differences is created and loaded into the inspection program for the on-the-fly method as a x-axis correction value and a y-axis correction value for each hole location. For each subsequent part with this unique part number inspected, the appropriate correction values will be added to the actual measured dimensional values thereby "correcting" for the output results from the on the fly inspection method disclosed herein to conform to the conventional "stop and dwell" method, whereby accuracy of measurement does not suffer, but significant time saving are achieved.

The terminology used herein is for the purpose of description, not limitation. Specific structural and functional details disclosed herein are not to be interpreted as limiting, but merely as basis for teaching one skilled in the art to employ the present invention. Those skilled in the art will also recognize the equivalents that may be substituted for elements described with reference to the exemplary embodiments disclosed herein without departing from the scope of the present invention.

While the present invention has been particularly shown and described with reference to the exemplary embodiment as illustrated in the drawing, it will be recognized by those skilled in the art that various modifications may be made without departing from the spirit and scope of the invention. For example, in the implementation of the inspection method described herein, the inspection measures the hole location in two dimensions. However, in other applications, the method could be used to measure hole size or the orientation of the axis of the hole relative to the surface of the airfoil. Therefore, it is intended that the present disclosure not be limited to the particular embodiment(s) disclosed as, but that the disclosure will include all embodiments falling within the scope of the appended claims.

We claim:

1. A method for inspecting a plurality of target features arrayed in spaced arrangement on a surface of a target object, comprising the steps of:
providing a fixture for holding the target object;
providing a high speed camera;
selectively positioning at least one of the holding fixture and the high speed camera relative to the other in a continuous relative motion along a three-dimensional path over a plurality of selected target features without pause; and
each time the high speed camera orientates to a selected target feature, capturing an image and determining a location of the selected target feature during an exposure duration using the high speed camera while in relative motion, the high speed camera enabling inspecting of the plurality of selected target features without pause, movement of the selected target feature relative to the high speed camera over a duration of a frame capture being less than a predetermined fraction of a true position tolerance of the selected target feature.

2. The method as recited in claim 1 further comprising the step of providing a position manipulator in operative association with the holding fixture for selectively positioning the holding fixture to orient a feature to be imaged on the target object to a desired orientation relative to the high speed camera at each selected target feature along the three dimensional path.

3. The method as recited in claim 1 further comprising the step of storing the captured image in a data archive and processing the captured image in parallel with relative movement of the high speed camera and the holding fixture from the imaged target feature to a next to be imaged target feature.

4. The method as recited in claim 1 further comprising the steps of:
providing a light array in operative association with the high speed camera; and
each time the high speed camera orientates to a selected target feature, powering the light array to illuminate the selected target feature during the exposure duration.

5. The method as recited in claim 4 wherein the step of providing a light array in operative association with the high speed camera comprises providing an array of a plurality of light emitting diodes in operative association with the high speed camera; and the step of powering the light array optionally includes selectively overpowering the light emitting diodes during the exposure duration.

6. The method as recited in claim 1 wherein the high speed camera has an exposure duration of less than about 3 milliseconds.

7. An inspection system for inspecting a plurality of target features arrayed in spaced arrangement on a surface of a target object, comprising:
a position manipulator having a fixture for holding the target object;
a high speed camera, the high speed camera having an exposure duration of less than 3 milliseconds and configured to at least in part capture an image and determine a location of the target features, the high speed camera enabling inspecting of the plurality of selected target features without pause, movement of the selected target feature relative to the high speed camera over a duration of a frame capture being less than a predetermined fraction of a true position tolerance of the selected target feature;
a light array in operative association with the high speed camera;
a controller operatively associated with the high speed camera and with the position manipulator; and
a processor operatively associated with the high speed camera for processing an image of a target feature received from the high speed camera.

8. The inspection system as recited in claim 7 wherein the high speed camera comprises a video camera having a frame rate capability of at least about 300 frames per second.

9. The inspection system as recited in claim 8 wherein the video camera has a frame rate capability of at least about 1000 frames per second.

10. The inspection system as recited in claim 7 wherein the light array includes a plurality of light emitting diodes.

11. The inspection apparatus as recited in claim 10 further comprising a LED driver operatively associated with the light emitting diodes for selectively switching the light emitting diodes from zero to full rated power in less than about 1 microsecond.

12. The inspection apparatus as recited in claim 10 wherein the LED driver has the capability of selectively switching the light emitting diodes from zero to a power level in excess of full rated power in less than about 1 microsecond.

13. A method for inspecting a turbine airfoil for measuring the location of at least of a plurality of selected holes of a multiplicity of holes arrayed in spaced arrangement in a surface of the turbine airfoil, comprising the steps of:
providing a position manipulator having a fixture for holding the turbine airfoil during inspection, the position manipulator having a 5-degree of freedom positioning system for selectively positioning the holding fixture to orientate the turbine airfoil;
providing a high speed camera having an exposure duration;
providing a plurality of light emitting diodes in operative association with the high speed camera;
selectively positioning at least one of the holding fixture and the high speed camera relative to the other in a continuous relative motion along a three-dimensional path over the plurality of selected holes without pause; and
each time the high speed camera orientates to a selected one of the plurality of selected holes, powering at least selected light emitting diodes of the plurality of the lighting emitting diodes to illuminate the selected hole at least for the exposure duration and capturing an image and determining a location of the selected hole during the exposure duration using the high speed camera while in relative motion with respect to the selected hole, the high speed camera enabling on-the-fly inspecting of the plurality of selected holes without pause, movement of the selected hole relative to the high speed camera over a duration of a frame capture being less than a predetermined fraction of a true position tolerance of the selected hole.

14. The method as recited in claim 13 wherein the high speed camera has an exposure duration of less than about 3 milliseconds.

15. The method as recited in claim 14 wherein the step of selectively positioning at least one of the holding fixture and the high speed camera relative to the other includes the step of simultaneously moving the high speed camera and repositioning the holding fixture in relative motion.

16. The method as recited in claim 14 wherein the high speed camera comprises a video camera having a frame rate of at least 300 frames per second and in relative motion with respect to a selected hole to be imaged at a relative speed of at least about 50 inches per minute.

17. The method as recited in claim 13 further comprising the step of storing the captured hole image in a data archive and processing the captured image in parallel with movement of the video camera from the imaged hole to a next selected hole to be imaged.

18. The method as recited in claim 13 wherein the step of powering at least selected light emitting diodes of the plurality of light emitting diodes comprises powering the selected light emitting diodes from zero power to at least full power in less than about 1 millisecond.

19. The method as recited in claim 13 further comprising the step of triggering the high speed camera to image a target feature when the high-speed camera and the target feature are aligned in gun barrel shot relationship.

20. The method as recited in claim 13 further comprising the step of probing the position of the turbine airfoil within the fixture, the step of probing including the steps of:
  setting a nominal location and orientation of a turbine airfoil loaded into the CNC machine to what was found as an actual location and orientation of a most previous turbine airfoil inspected; and
  initially probing a selected single point on the turbine airfoil to establish an estimate of the turbine airfoil location along the part Z-axis.

* * * * *